United States Patent [19]

Bron

[11] Patent Number: 5,584,314

[45] Date of Patent: Dec. 17, 1996

[54] SELF-CLEANING INLET HEAD FOR A FLUID

[76] Inventor: Dan Bron, 39/47 Soroka Street, Haifa 34759, Israel

[21] Appl. No.: 500,150

[22] Filed: Jul. 10, 1995

[30] Foreign Application Priority Data

Jul. 12, 1994 [IL] Israel ........................ 110,288

[51] Int. Cl.⁶ ........................ A61M 5/00; F16K 15/02
[52] U.S. Cl. ........................ 137/239; 137/244; 137/512;
137/516.27; 137/538; 137/540; 137/543.17;
210/131; 210/136; 210/408; 210/411; 210/427;
604/8; 604/9; 604/247
[58] Field of Search ........................ 137/239, 244,
137/512, 516.27, 538, 540, 543.17; 15/104.011,
104.061; 210/131, 136, 408, 411, 427,
429; 222/148; 604/8, 9, 247

[56] References Cited

U.S. PATENT DOCUMENTS

| | | | |
|---|---|---|---|
| 1,049,012 | 12/1912 | Weber et al. | 137/239 |
| 2,377,595 | 6/1945 | Wiles | 137/239 |
| 2,793,752 | 5/1957 | Jay | 210/429 |
| 3,550,624 | 12/1970 | Johnson | 137/239 |
| 3,557,820 | 1/1971 | Jackson et al. | 137/239 |
| 4,375,821 | 3/1983 | Nanao | 137/239 |
| 4,442,859 | 4/1984 | Gentry | 137/239 |
| 4,508,138 | 4/1985 | Dixon | 137/239 |
| 4,560,375 | 12/1985 | Schulte et al. | 604/9 |
| 4,573,492 | 3/1986 | Tadokoro | 137/239 |
| 4,650,463 | 3/1987 | LeVeen et al. | 604/43 |
| 4,811,230 | 3/1989 | Gerulis | 210/411 |
| 5,042,522 | 8/1991 | Corenman et al. | 137/239 |
| 5,054,518 | 10/1991 | Rancani | 137/516.27 |

FOREIGN PATENT DOCUMENTS

WO 83/01387  4/1983  WIPO.

*Primary Examiner*—George L. Walton
*Attorney, Agent, or Firm*—Larson and Taylor

[57] ABSTRACT

The invention provides a self-cleaning inlet head for a fluid, operable in a first, draining, mode and in a second, back-flushing, mode, including a body having a front end and a rear end; a piston slidably mounted in the body and having having a front face and a rear face; a first space extending between the rear end of the body and the rear face of the piston and a second space extending between the front face of the piston and the front end of the body; a bore connecting the first space and the second space; a valve mounted in the first space for closing off the bore during the second mode of operation; an aperture for access of the fluid from outside the head into the second space in the first mode of operation, and for exit from the second space in the second mode of operation, wherein, at the onset of the second mode of operation, the valve closes off the bore and subsequently moves the piston, thereby initiating a mechanical shearing action loosening any occluding matter in the aperture. The mechanical action is followed by an hydraulic flushing action.

8 Claims, 1 Drawing Sheet

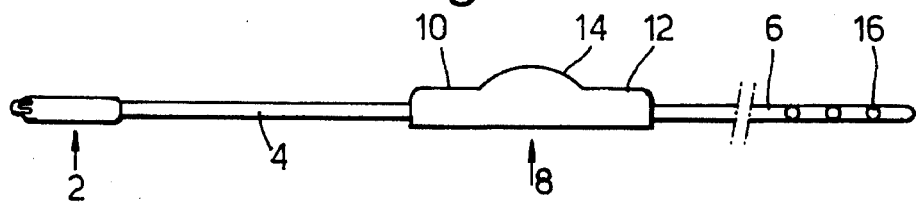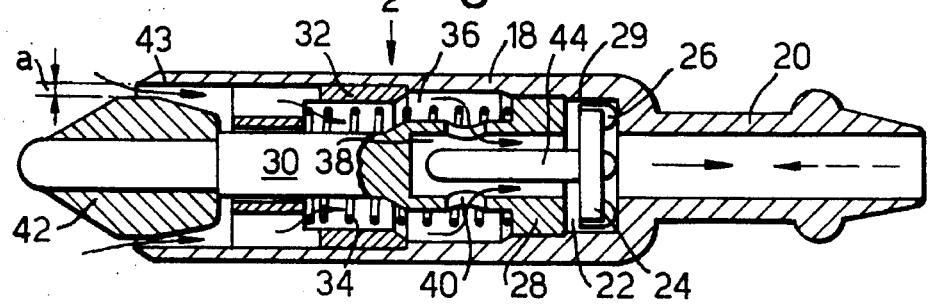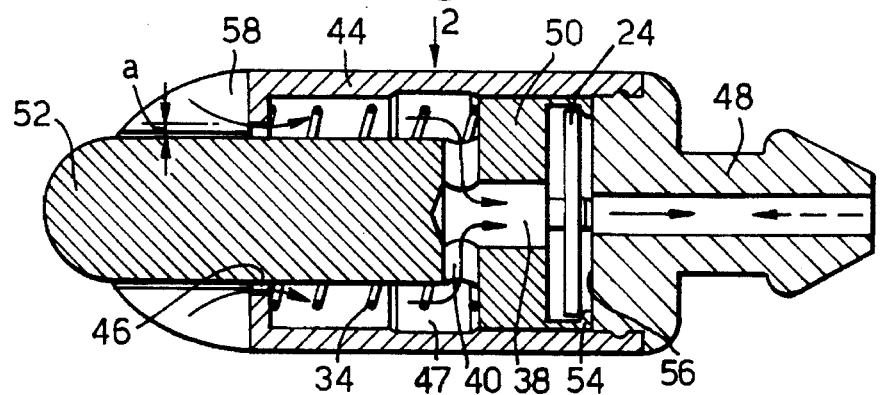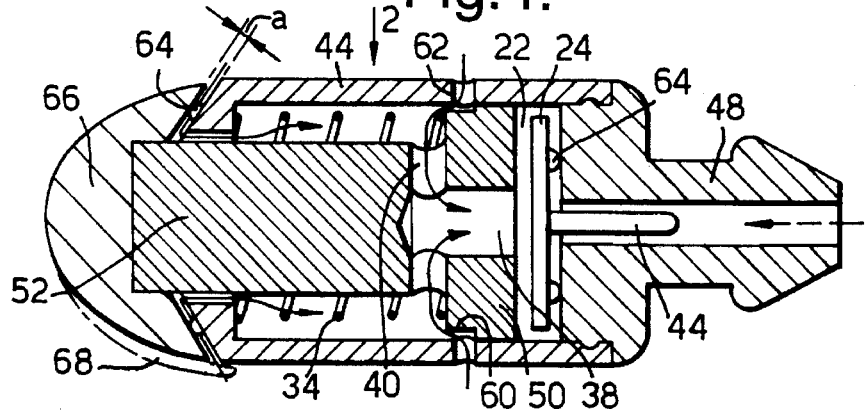

SELF-CLEANING INLET HEAD FOR A FLUID

The present invention relates to a self-cleaning inlet head for a fluid, in particular for a cerebrospinal fluid (CSF) shunt used in the treatment of hydrocephalus.

Hydrocephalus is a condition in which, either due to overproduction of CSF or due to obstruction in the drainage system thereof, the amount of CSF within the cranial cavity increases abnormally, greatly enlarging the ventricular spaces and thereby producing harmful pressure on the brain itself.

While at the present time there exists no definite cure for hydrocephalus, some surgical procedures are known which enable most patients to lead normal lives.

One of these procedures consists of the surgical implanting of a duct or shunt system, leading from the lateral ventricle of the brain into a body cavity (such as the abdominal cavity) where the excess CSF can be absorbed. The shunt system comprises a proximal catheter to be introduced into the ventricle, a compressible, valved reservoir to be implanted below the skin, usually behind the ear and connected to the proximal catheter, and a distal catheter connected to the other end of the reservoir and leading into the above-mentioned body cavity. Through small apertures in the tip of the proximal catheter, the excess CSF can enter the shunt, to be drained via apertures in the end of the distal catheter into the body cavity.

Shunt procedures are not without complications, the most common of which is obstruction of the system. Obstruction or clogging may take place at any point along the shunt, but most frequently occurs at the very small apertures of the ventricular end of the shunt, where brain and other tissue is present. When clogging occurs, an attempt is made to remove the obstructing matter by backflushing, using the CSF present in the compressible reservoir. However, due to the smallness of the apertures at the ventricular end and due to the small amount of flushing liquid available, these attempts are not always successful with the known shunt systems and one or more surgical shunt revisions are often required.

It is thus one of the objects of the present invention to provide a self-cleaning inlet head for the ventricular end of a CSF shunt that, by combining mechanical and hydraulic action, will effectively loosen and sweep away the most stubbornly clinging matter.

According to the invention, this is achieved by providing a self-cleaning inlet head for a fluid, operable in a first, draining, mode and in a second, backflushing, mode, comprising a substantially cylindrical body having a front end and a rear end, said rear end having means for connection to a draining and backflushing tube; piston means slidably mounted in said body and having a piston rod extending towards said front end, said piston means having a position of rest towards which it is urged by a biasing spring, said piston means having a front face facing said front end and a rear face facing said means for connection; a first space extending between said means for connection and the rear face of said piston means, and a second space extending between the front face of said piston means and the front end of said body; at least one bore at least passing through said piston means and connecting said first space and said second space; valve means mounted in said first space and provided with means preventing it from closing off said means for connection to said draining and backflushing tube during said first mode of operation, but permitting it to close off said at least one bore connecting said first and said second space during said second mode of operation; at least one aperture as a means for access of said fluid from outside of said head into said second space whilst being strained in said first mode of operation, and for exit from said second space whilst flushing said at least one aperture in said second mode of operation, wherein at least on the onset of said second mode of operation, said valve means closes off said at least one bore and subsequently moves said piston means and said piston rod, thereby initiating a mechanical shearing action loosening any occluding matter in said at least one aperture, said mechanical action being followed by a hydraulic flushing action.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a general view of a CSF shunt carrying a head according to the invention;

FIG. 2 is a cross-sectional view, to a greatly enlarged scale, of a preferred embodiment of the head according to the invention;

FIG. 3 represents another embodiment of the head, and

FIG. 4 shows yet another embodiment of the head.

Referring now to the drawings, there is seen in FIG. 1 a CSF shunt comprising, apart from the CSF inlet head 2, a proximal catheter 4, a distal catheter 6, a reservoir 8 made of a pliable material to which both the proximal and the distal catheters 4 and 6 are connected, and which includes an inlet occluder 10 which is a kind of valve that, when depressed, blocks off the proximal catheter 4, and an outlet occluder 12 that, when depressed, blocks off the distal catheter 6.

Further seen is a pump dome 14, a blister-like projection that, when depressed, displaces part of the fluid volume of the reservoir, either towards the head 2 when the outlet occluder 12 is depressed, or towards the drainage apertures 16 at the end of the distal catheter 6, when the inlet occluder 10 is depressed. Flushing of head 21 is thus carried out by first depressing outlet occluder 12 and then pump dome 14, while flushing outlet apertures 16 is performed by first depressing inlet occluder 10 and then pump dome 14.

FIG. 2 represents a preferred embodiment of the invention.

There is seen a substantially cylindrical body 18, provided with a neck portion 20 serving as a connector to be pushed into proximal catheter 4. FIG. 2 is obviously drawn to a greatly enlarged scale, with the true outside diameter of body 18 beinbg about 3.5 mm. Body 18, advantageously made of a plastic material such as polypropylene, is hollow and provided with a stepped bore, the smallest diameter of which is located within the neck portion 20. The next larger, adjacent diameter defines a space 22, which accommodates a disk-shaped valve 24 having several peripheral projections 26 that prevent it from ever closing off the bore of neck portion 20.

To the left of valve 24 there is seen a piston 28, abutting in its position of rest (as shown) against a shoulder 29 at the edge of space 22. Piston 28 is freely sliding in body 18 and is provided with a piston rod 30 guided by a slotted cup 32 fixedly seated in the widest portion of the bore of body 18.

Abutting against the bottom of cup 32 on one end and against piston 28 on the other, there is seen a helical spring 34 advantageously made of a fine stainless-steel wire, which biases piston 28 against shoulder 29.

For a purpose to be explained further below, the portion of the bore of body 18 located between piston 28 (in its position of rest, as shown) and the edge of cup 32 has a diameter larger by, for example, about 0.2 mm than the diameter of piston 28, defining a space 36.

It is further seen that piston 28 is provided with a bore 38 which, via holes 40, communicates with space 36.

The end of piston rod 30 is slightly stepped down and carries a head piece 42 tapered and smoothly rounded to facilitate surgical insertion into a ventricular cavity of the brain. It is also seen that head piece 42 has a somewhat smaller diameter than the bore of body 18 at this spot, thus creating an annular gap a which in reality is about 0.2 to 0.3 mm. The rear portion of head piece 42 is also tapered. Due to this rear taper, the size of the gap increases when head piece 42 advances during backflushing, thus facilitating cleaning.

Valve 24 is provided with a guide pin 44 loosely guided in bore 38. Instead of projecting into bore 38, such a pin could also be attached to the other face of valve 24 and extend into the bore of neck portion 20.

During normal drainage operation, the excess CSF enters head 2 through the annular gap a in direction of the solid arrows and, via the slots in the slotted cup 32, space 36, holes 40, bore 38 and space 22, reaches connector 20 and proximal catheter 4 (FIG. 1), whence it continues via reservoir 8 and distal catheter 6 into the already mentioned body cavity, where it is absorbed.

Clogging of the inlet to head 2 or blockage of holes 16 in distal catheter 6 (FIG. 1) will, within a very short period of time, produce clearly perceptive symptoms, at which point attempts must be made to remove the obstructions. This is done in the following way:

By applying pressure to outlet occluder 12, distal catheter 6 is blocked. Then pump dome 14 is depressed, causing part of the CSF in reservoir 8 to be forced back into head 2, as indicated by the dashed arrow. As a consequence of this back flow, valve 24 is pushed back, at first closing off the entrance into bore 38. With the pressurized fluid from reservoir 8 continuing to act, the pressure causes the entire piston assembly (piston 28, piston rod 30 and head piece 42) to move to the left, producing a relative movement between the head piece 42 and the rim 43 of body 18, whilst compressing spring 34. At this stage, it is the shearing action produced by this mechanical movement that loosens the debris which to some degree has filled gap a. In the meantime, piston 28 continues to advance until, at a certain moment, it will be fully inside space 36, the outside diameter of which, it will be remembered, is larger than the diameter of piston 28. At that moment, the pressurized CSF from space 22 shoots forward, passing rapidly into space 36 and, via slotted cup 32, impacts and removes the already loosened debris in gap a. It is thus the combination of mechanical and hydraulic action that produces the improved cleaning effect. As a sign of successful cleaning, the depressed pump dome 14, when released, will rise to its original height (while outlet occluder 12 is still held down). Spring 34 will restore piston 28 to its position of rest.

A further embodiment is shown in FIG. 3. Here, the head body consists of two parts held together by a snap-in joint, namely, a sleeve 44 with a circular inlet opening 46 and a neck portion 48. Sleeve 44 has a stepped internal diameter, with the diameter of the central portion 47 being slightly larger than that of the two other portions, as can be seen. Adjacent to neck portion 48 there is seen, in its position of rest, a piston 50 with which is integral a piston rod 52. The latter passes through inlet opening 46, turning this opening into an annular gap a which has the same function as had the gap of the previous embodiment.

Piston 50 is provided with an axial bore 38 which communicates with the space defined by the inside wall of sleeve 44 via holes 40. Piston 50 also carries a plurality of fingers 54 with which it abuts against faces 56 of neck portion 48. Fingers 54 also serve to retain a disk-shaped valve 24, made here of an elastomer, which has the same functions as valve 24 of the previous embodiment, except that, being held in a concentric position by finger 54, it has no need for a guide rod.

Also seen is the helical spring 34 which under normal drainage conditions biases piston 50 towards its position of rest, as shown. Fingers 54 also prevent valve 24 from closing off the bore of neck portion 48.

Sleeve 44 has a domed end 58 provided with a plurality of slots which facilitate access of the CSF to the gap a, while the fingers produced by slotting serve as guide to piston rod 52, also preventing contact of tissue with gap a, liable to clog the latter.

The operation of this embodiment is analogous to that of the previous embodiment. Upon actuation of pump dome 14 (FIG. 1), the backflushing fluid (dashed arrow) causes valve 24 first to close off bore 38, and then to move piston 50 and piston rod 52 towards the left, producing at first the above-explained mechanical shearing action and subsequently, when piston 50 has advanced into the widened section of the inside wall of sleeve 44, producing a rush of backflushing fluid which sweeps away the debris previously loosened by the mechanical action.

Still another embodiment is shown in FIG. 4. Here, piston 50 has a peripheral portion 60 stepped down to a depth of 0.2-0.3 mm, opposite which (in the rest position of piston 50) sleeve 44 is provided with a plurality of radial holes 62 which constitute the major strainer of head 2. The position of rest of piston 50 is defined by abutment projections 64 located on the conical end face of sleeve 44, against which projections abuts a head piece in the form of a rounded cap 66 fixedly attached to piston rod 52. The above conical end face defines with the inner face of cap 66 a conical annular gap a, constituting in this embodiment one of the two straining possibilities provided, the other being the plurality of holes 62. The conical gap a is intended to prevent chafing and pinching of brain tissue during introduction of the shunt. The protective effect of gap a can be enhanced by the addition, as integral parts of cap 66, of a number of ribs 68 which, during movement of head 2, keep the brain tissue away from gap a. Such ribs could also be an integral part of head piece 42 of the embodiment of FIG. 2.

The guided valve 24, also made of an elastomer, is here provided with projections 64 to prevent it from closing off the outlet bore of neck portion 48.

Action is mostly analogous to that described above in conjunction with the two previous embodiments. Backflushing (dashed arrow) first produces a shearing effect as piston rod 52 moves relative to the end of sleeve 44 and as the larger-diameter portion of piston 50 moves across holes 62. When piston 50 has moved so far to the left that holes 62 begin to communicate with space 22 which is full of pressurized CSF, the latter rushes foward, flushing holes 62 as well as gap a.

Valve 24 and guide pin 44 are here made of an elastomer, although they could also be made of a plastic material.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A self-cleaning inlet head for a fluid, operable in a first, draining, mode and in a second, backflushing, mode, comprising:

a substantially cylindrical body having a front end and a rear end, said rear end having means for connection to a draining and backflushing tube;

piston means slidably mounted in said body and having a piston rod extending towards said front end, said piston means having a position of rest towards which it is urged by a biasing spring, said piston means having a front face facing said front end and a rear face facing said means for connection;

a first space extending between said means for connection and the rear face of said piston means, and a second space extending between the front face of said piston means and the front end of said body;

at least one bore at least passing through said piston means and connecting said first space and said second space;

valve means mounted in said first space and provided with means preventing it from closing off said means for connection to said draining and backflushing tube during said first mode of operation, but permitting it to close off said at least one bore connecting said first and said second space during said second mode of operation;

at least one aperture as a means for access of said fluid from outside of said head into said second space whilst being strained in said first mode of operation, and for exit from said second space whilst flushing said at least one aperture in said second mode of operation, wherein, at least at the onset of said second mode of operation, said valve means closes off said at least one bore and subsequently moves said piston means and said piston rod, thereby initiating a mechanical shearing action loosening any occluding matter in said at least one aperture, said mechanical action being followed by a hydraulic flushing action, as soon as said piston means has moved from said first space into said second space.

2. The inlet head as claimed in claim 1, further comprising a head piece attached to said piston rod, defining said at least one aperture together with said front end of said body.

3. The inlet head as claimed in claim 2, wherein said at least one aperture is an annular gap.

4. The inlet head as claimed in claim 3, wherein said annular gap is conical.

5. The inlet head as claimed in claim 1, further comprising a second means of access of said fluid in the form of peripheral holes leading from the outside of said body into said second space.

6. The inlet head as claimed in claim 1, wherein said valve means is provided with a plurality of projections preventing it from closing off said means of connection.

7. The inlet head as claimed in claim 1, wherein said rear face of said piston means is provided with a plurality of finger-like projections maintaining said valve means in a position remote from said means of connection.

8. The inlet head as claimed in claim 1, further comprising a plurality of ribs integral with said head piece.

* * * * *